United States Patent
Richard

(10) Patent No.: US 8,109,762 B2
(45) Date of Patent: Feb. 7, 2012

(54) DENTAL HANDPIECE WITH ABUTMENT DEVICE

(75) Inventor: Hervé Richard, Notre Dame de Bellecombe (FR)

(73) Assignee: Anthogyr, Sallanches (FR)

( * ) Notice: Subject to any disclaimer, the term of this patent is extended or adjusted under 35 U.S.C. 154(b) by 263 days.

(21) Appl. No.: 12/444,175

(22) PCT Filed: Oct. 4, 2007

(86) PCT No.: PCT/IB2007/054045
§ 371 (c)(1),
(2), (4) Date: Apr. 3, 2009

(87) PCT Pub. No.: WO2008/041198
PCT Pub. Date: Apr. 10, 2008

(65) Prior Publication Data
US 2010/0047737 A1    Feb. 25, 2010

(30) Foreign Application Priority Data
Oct. 6, 2006 (FR) .................................. 06 54131

(51) Int. Cl.
*A61C 3/00* (2006.01)
*A61C 1/10* (2006.01)

(52) U.S. Cl. ................................ 433/75; 433/114

(58) Field of Classification Search .............. 433/75, 433/72, 102, 114, 116, 127, 128; 408/241 S; 82/153
See application file for complete search history.

(56) References Cited

U.S. PATENT DOCUMENTS

| | | | | |
|---|---|---|---|---|
| 3,346,959 A | * | 10/1967 | Fridge | 433/76 |
| 3,838,517 A | * | 10/1974 | Michnick | 433/72 |
| 4,571,183 A | * | 2/1986 | Nash | 433/116 |
| 4,778,387 A | * | 10/1988 | Komatsu | 433/116 |
| RE35,147 E | * | 1/1996 | Apap et al. | 433/102 |
| 6,213,770 B1 | | 4/2001 | Kuhn | |

FOREIGN PATENT DOCUMENTS

| | | |
|---|---|---|
| DE | 1084870 | 7/1960 |
| FR | 2831050 A1 | 4/2003 |

* cited by examiner

*Primary Examiner* — Cris L Rodriguez
*Assistant Examiner* — Heidi M Eide
(74) *Attorney, Agent, or Firm* — William H. Eilberg

(57) ABSTRACT

A dental handpiece carries a drill and drives it in relative motion in a direction of penetration. The handpiece includes a body with a proximal end and a distal end, a removable head connected to the body's distal end, able to hold the drill, abutment means fixed on the dental handpiece by fixation means and able to limit the depth of penetration of the drill in the body of a patient. The abutment means, protruding from the dental handpiece, are fixed and locked on the dental handpiece by locking means which are actuated by the simple movement of joining the head to the body.

10 Claims, 5 Drawing Sheets

DENTAL HANDPIECE WITH ABUTMENT DEVICE

TECHNICAL FIELD OF THE INVENTION

The present invention concerns the handpieces used by dentists and oral surgeons. More particularly, the invention concerns a dental handpiece for carrying a drill and driving it in relative movement in a penetration direction in order to drill into the maxillary or mandibular bone of a patient to insert a dental implant therein.

During the drilling, the practitioner passes his drill through several bony areas of different densities. The practitioner must pass through surface cortical bone areas and deeper spongy bone areas. The cortical bone being more difficult to drill, the practitioner is then obliged to apply a high axial force on the dental handpiece when he is drilling the surface bony areas. On sudden passage of the drill into a spongy bone area, the practitioner does not reduce instantaneously the axial force on the dental handpiece, and this can lead to exceeding the initially intended drilling depth. This accidental overshoot can result in cutting of the dental nerve and partial or complete desensitization of the surrounding area.

A first solution for avoiding this accidental cutting of the dental nerve was to use a dental handpiece fitted with a drill having a plurality of markings or annular grooves along its length. The practitioner then monitors the penetration of the drill by reading off these markings or annular grooves. However, the presence of blood and/or saliva in the vicinity of the working area of the drill prevents reliable reading of the markings on the drill. Such a solution is therefore not reliable.

A second solution for avoiding this accidental cutting of the dental nerve was to use dental handpieces for carrying a drill and driving it in relative movement in a penetration direction, comprising:
  a body with a proximal body end and a distal body end,
  a head connected to the distal body end, adapted to hold the drill,
  abutment means fixed to the dental handpiece by fixing means and limiting the depth of penetration of the drill into the body of a patient,
  wherein the abutment means comprise an abutment body with a bearing surface adapted to bear against the body of the patient at the end of penetration of the drill into the body of the patient.

Such a handpiece is described in the document FR 2 831 050 among others.

The drawback of these handpieces is that the abutment means fixed to the dental handpiece have a large overall size liable to impede the practitioner during his operation. Thus the practitioner cannot access certain areas to be treated of the mouth of the patient, access to which is difficult. This impediment to the practitioner can also result in unnecessary pains for the patient or in a lack of precision in the surgical operation carried out in this way.

Moreover, these abutment means are difficult or even impossible to demount, and thus impede the practitioner during other operations in which the practitioner has no need of the abutment means.

Moreover, the abutment means of such handpieces make the operations of cleaning the various elements constituting them complicated, through dismantling that is often long and laborious and sometimes incites the practitioner to clean the dental handpieces only partly or superficially.

Another solution for avoiding accidental cutting of the dental nerve was to use drills provided with a shoulder serving as an abutment at the end of penetration of the drill into the body of the patient. The drawback is that such drills can be used to fit only one length of implant, their abutment means being by nature non-adjustable. The practitioner then has to have recourse to a large number of drills for drilling to different depths. This results in a non-negligible hardware cost for the practitioner, for whom the number of tools necessary for carrying out his work correctly increases, and who must change tool more frequently.

Using dental handpieces of the type from the document FR 2 831 050 complicates the use of drills with abutment shoulders because of the overall size of the abutment means, which are furthermore of no utility. The practitioner is thus impeded without benefit, which risks causing the patient unnecessary pains or leads to lack of precision during the operation to be carried out.

Another system for making drilling operations reliable that has been envisaged uses a surgical guide provided with drilling bushes and intended to be used with drills having no abutment shoulder.

It is these drilling bushes that serve as abutment for the drill, as a function of the length selected. However, using a surgical guide is impossible with a dental handpiece such as that described in the document FR 2 831 050 because of the overall size of the abutment means in the vicinity of the head of the dental handpiece.

There is also known a handpiece, such as that described in the document U.S. Pat. No. 6,213,770, that includes abutment means rendered removable by means of a reversible engagement such as clipping. There is however a risk of the abutment means being accidentally detached and/or moving relative to the dental handpiece while it is being used in the mouth. This results in a lack of reliability that is unacceptable for practitioners.

SUMMARY OF THE INVENTION

A first problem proposed by the present invention is to design reliable abutment means that are easy to clean, of compact overall size, easily and quickly fitted to a dental handpiece to make drilling operations carried out with a drill having no abutment shoulder reliable and also enabling easy use of a drill comprising an abutment shoulder or the use of a surgical guide with drilling bushes.

Another aspect of the invention aims to limit the overall size of the abutment means so as not to impede the practitioner when he does not need to use the abutment means.

Simultaneously, the invention further aims to design abutment means that are simple and quick to fit to the dental handpiece, necessitate very little modification of the dental handpiece in order to mount them thereon, and are adapted to be fixed to or detached from the dental handpiece only when the latter is not operating.

To achieve the above and other objects, the invention proposes a dental handpiece for carrying a drill and driving it in relative movement in a penetration direction, comprising:
  a body with a proximal body end and a distal body end,
  a demountable head, connected to the distal body end, adapted to hold the drill,
  abutment means fixed to the dental handpiece by fixing means and limiting the depth of penetration of the drill into the body of a patient,
  wherein the abutment means comprise:
  an abutment body with a bearing surface adapted to bear against the body of the patient at the end of penetration of the drill into the body of the patient, a connecting section fastened to the abutment body and extending in a direction substantially perpendicular to the bearing surface, a guide support forming a projection on the dental handpiece, adapted to hold the connecting section, and including at least one projecting part which is an attached part detachably fixed to the dental handpiece, wherein:

the fixing means comprise a female cavity produced in the dental handpiece, the fixing means comprise a male protuberance fastened to the abutment means and conformed to penetrate and to be retained in the female cavity, the dental handpiece includes locking means that selectively prevent separation of the male protuberance and the female cavity and that are actuated by the simple movement of assembling the head onto the body.

This provides the practitioner with a number of modes of use between which he can choose at will: either he fits the abutment means to use a drill with or without an abutment shoulder, or he reduces the overall size of the dental handpiece by removing at least part of the abutment means when he does not need them, then using a drill with an abutment shoulder, or a surgical guide with drilling bushes with a drill having no abutment shoulder.

To detach the abutment means, it is necessary to separate the head from the body of the dental handpiece. Such separation is impossible when the dental handpiece is operating. There is thus no risk of unintentional and accidental demounting of the abutment means when the practitioner is operating on the patient.

The guide support can preferably be entirely detachable from the dental handpiece, in order to remove all elements forming a projection on the dental handpiece. This imparts a minimum overall size to the dental handpiece in order not to impede the practitioner when he has no need of the abutment means.

The female cavity is advantageously produced in the vicinity of the head and is conformed to allow engagement of the male protuberance in an engagement direction substantially perpendicular to the penetration direction and to prevent any extraction of the male protuberance in any direction other than the engagement direction.

Such fixing means allow mounting and fixing of the abutment means on and to the dental handpiece by a simple fast movement in translation and without having recourse to tools.

In a preferred embodiment of the invention, it can be provided that:

the head can be removably fixed to the distal body end by axial engagement in the distal body end, the female cavity can be produced on the head, oriented axially in the engagement direction and open at its proximal end, the locking means can comprise an abutment facet, disposed at the distal body end, which blocks the proximal end of the female cavity once the head has been assembled onto the body, the male protuberance of the fixing means can extend over a length equal to or slightly less than the length of the female cavity.

Thus the male protuberance is retained in the female cavity only by the connection of the head to the distal body end, without necessitating any other part. The locking means and the fixing means are very simple, including few parts and able to be produced economically on existing dental handpieces without necessitating particular adaptation.

The female cavity can preferably be a groove and the male protuberance can preferably be a rib.

BRIEF DESCRIPTION OF THE DRAWINGS

Other objects, features and advantages of the present invention will emerge from the following description of particular embodiments, given with reference to the appended figures, in which.

DESCRIPTION OF PREFERRED EMBODIMENTS

Figure 7:
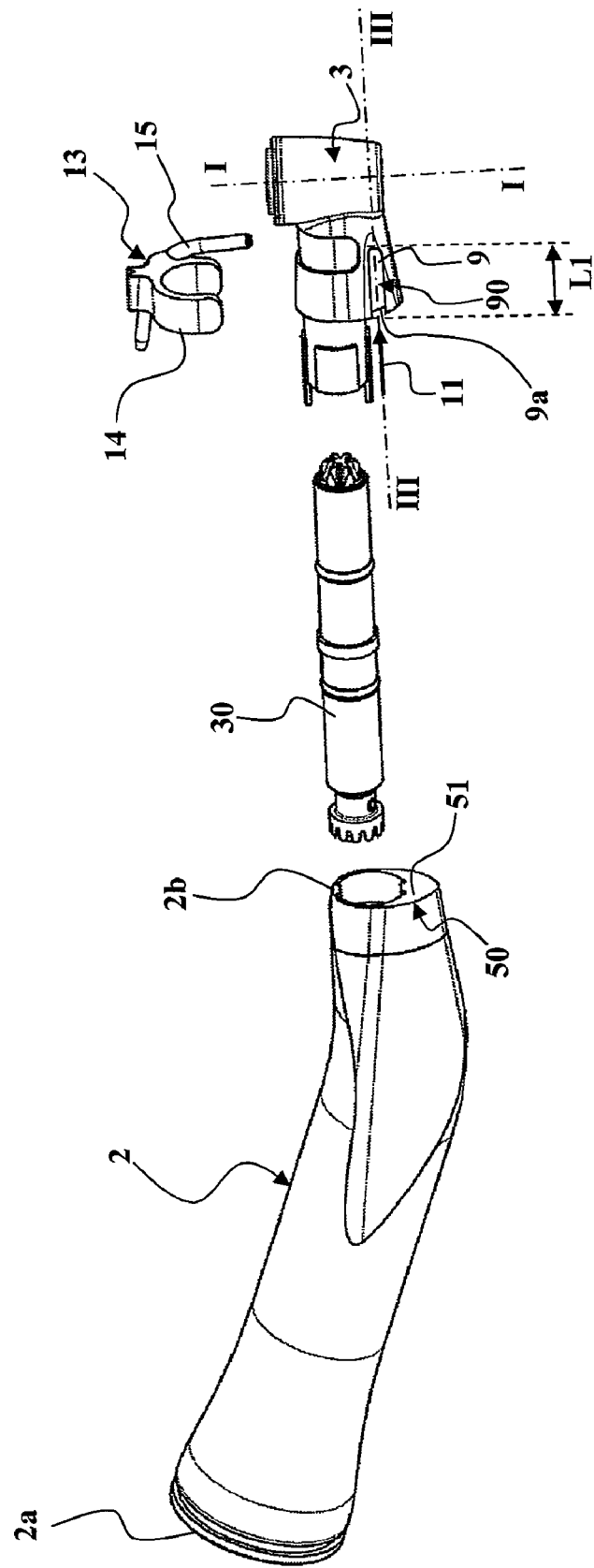
FIG. 7 is a perspective view of the various components constitutive of the dental handpiece of the invention.

As represented in FIG. 7, the dental handpiece includes in the usual way a body 2 with a proximal end 2a and a distal end 2b and a demountable head 3 adapted to be connected to the distal body end 2b and to hold a drill.

Figure 1:
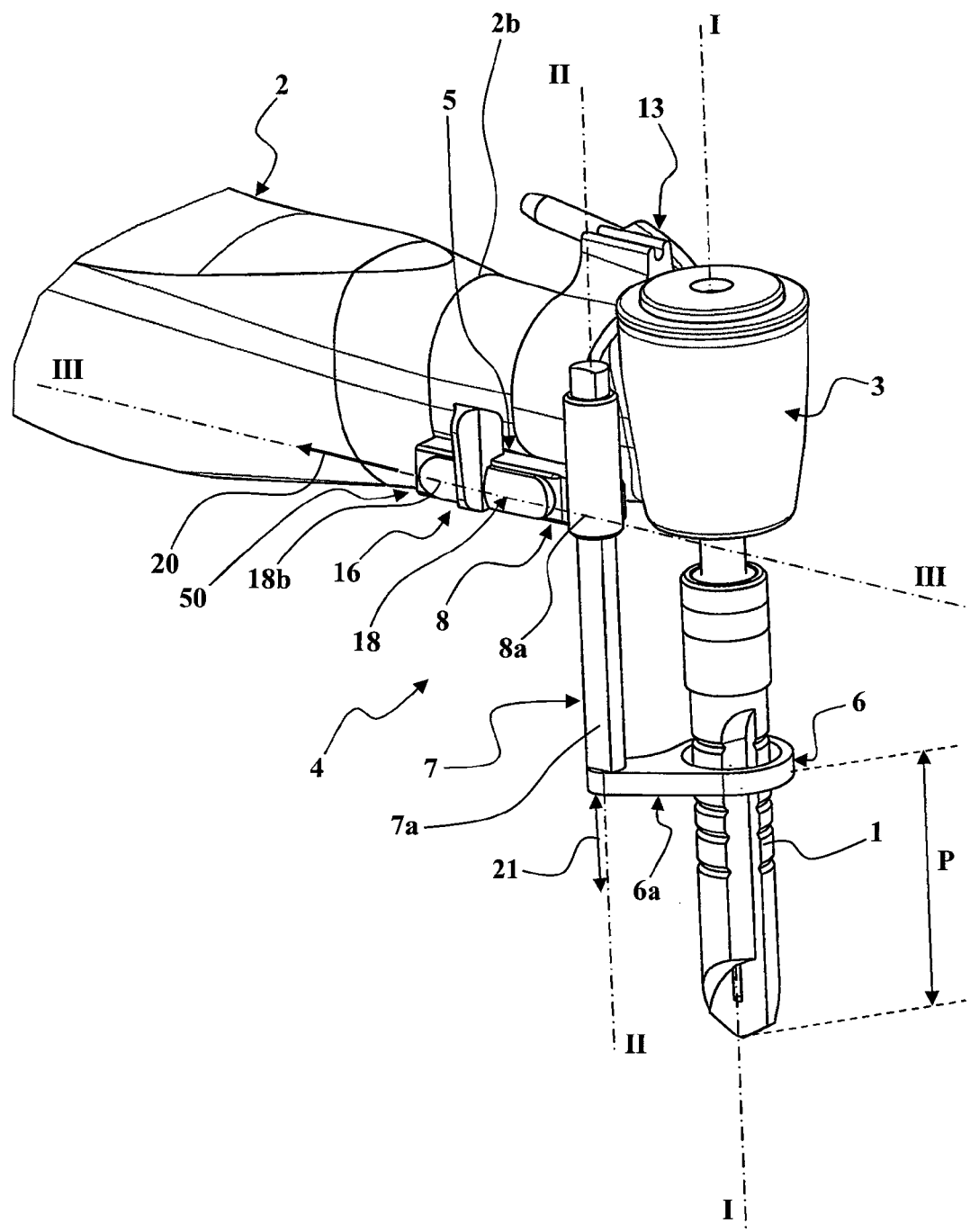
FIG. 1 is a perspective view of a dental handpiece conforming to one embodiment of the invention, with a drill having no abutment shoulder.

In FIG. 1, the dental handpiece carries a drill 1 with no abutment shoulder. The dental handpiece can drive the drill 1 in relative movement in a penetration direction I-I. The dental handpiece includes abutment means 4 that are fixed to the dental handpiece by fixing means 5 to limit the depth of penetration of the drill 1 into the body of the patient.

The abutment means 4 comprise:

an abutment body 6 with a bearing surface 6a adapted to bear against the body of the patient at the end of penetration of the drill 1 into the body of the patient, a connecting section 7 fastened to the abutment body 6 and extending in a direction II-II substantially perpendicular to the bearing surface 6a, a guide support 8, forming a projection on the dental handpiece, adapted to hold the connecting section 7. At least one projecting part of the guide support 8 is an attached part fixed to the dental handpiece in a detachable fashion.

Figure 3:
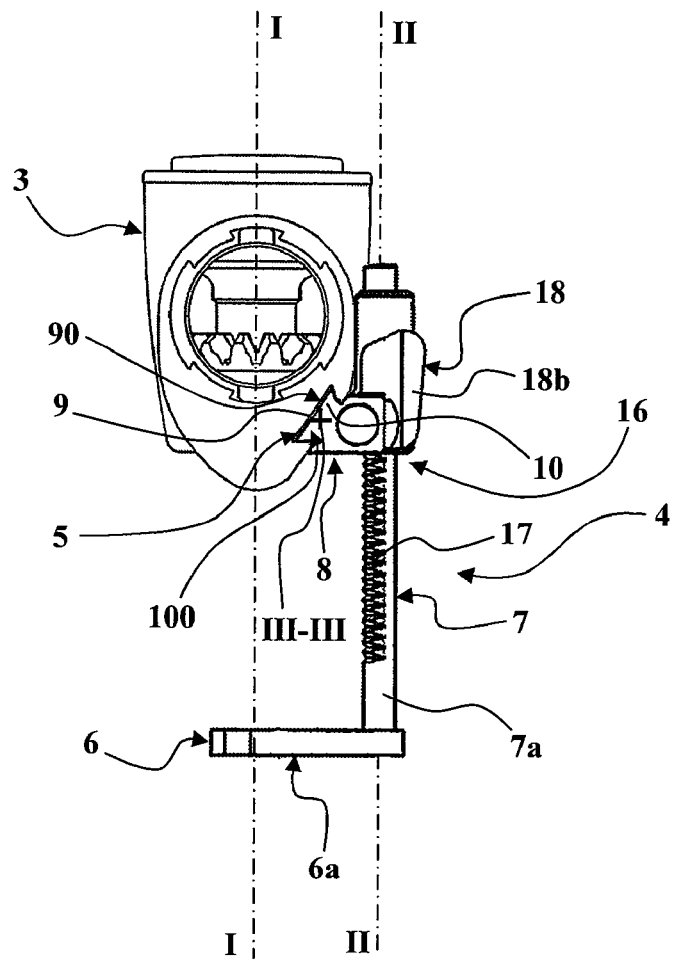
FIG. 3 is a view in cross section of the dental handpiece from FIG. 1.

It is seen more particularly in FIG. 3 that in the embodiment that is shown the guide support 8 is entirely detachable from the dental handpiece, which minimizes the overall size of the dental handpiece when the abutment means 4 are of no utility.

Figure 2:
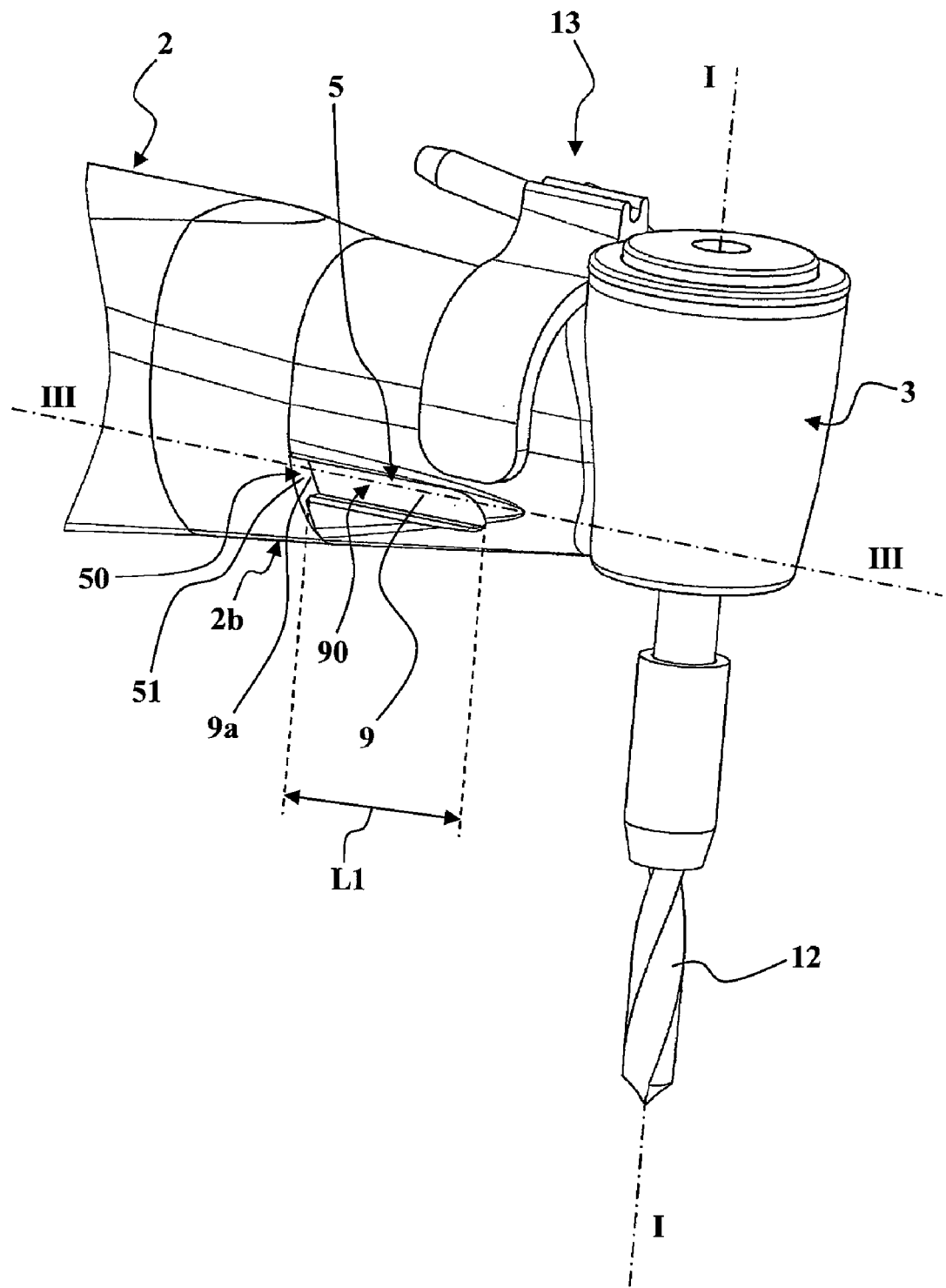
FIG. 2 is a perspective view of the dental handpiece from FIG. 1, when using a drill with an abutment shoulder.

The means 5 for fixing the abutment means 4 to the dental handpiece comprise a female cavity 90 produced in the dental handpiece in the vicinity of the head 3 (FIG. 2). The fixing means 5 also comprise a male protuberance 100 (FIGS. 3 and 4), fastened to the abutment means 4, conformed to penetrate into and to be retained in the female cavity 90.

The dental handpiece includes locking means 50 that selectively prevent separation of the male protuberance 100 and the female cavity 90 and that are actuated entirely by the movement of fitting the head 3 onto the body 2.

The locking means 50 are of simple design and simple to use and are necessary and sufficient to prevent any unintentional and accidental demounting of the abutment means 4 while the practitioner is using his dental handpiece to operate on a patient.

The female cavity 90 is conformed to allow the engagement of the male protuberance 100 in an engagement direction III-III substantially perpendicular to the penetration direction I-I and to prevent extraction of the male protuberance 100 in any direction other than the engagement direction III-III.

Such fixing means 5 allow the support 8 of the abutment means 4 to be mounted by simple movement in axial translation as illustrated by the arrow 11 in FIG. 7. The mounting of the abutment means 4 on the dental handpiece can therefore be effected by the practitioner, simply and quickly and without having recourse to tools.

As seen more particularly in FIG. 7, the head 3 is demountable and can be removably fixed to the distal end 2b of the body 2 by axial engagement in the distal end 2b of the body 2. The transmission shaft 30 is housed partly in the body 2 and partly in the head 3, in a manner that is known in the art. The female cavity 90 is produced on the head 3, over a length L1, oriented axially in the engagement direction III-III and opened at its proximal end 9a.

The locking means 50 comprise an abutment facet 51 disposed at the distal end 2b of the body 2.

Once the head 3 has been assembled to the body 2, the locking means 50 (abutment facet 51) close the proximal end 9a of the female cavity 90 (FIG. 2), thus preventing all risk of the male protuberance 100 escaping from the female cavity 90.

The locking means 50 are actuated by the sole necessary and sufficient movement of assembling the head 3 onto the body 2.

In another embodiment of the invention (not shown), the female cavity 90 is produced partly in the head 3 and partly in the body 2, assembling the head 3 and the body 2 forming a closed female cavity 90 adapted to retain the male protuberance 100. The male protuberance is then retained simultaneously in the head 3 and in the body 2.

In the particular embodiment shown in FIGS. 1 to 7, the female cavity 90 and the male protuberance 100 are a groove 9 and a rib 10 that have trapezoidal cross sections of complementary shape constituting a dovetail joint.

The trapezoidal cross sections of complementary shape of the groove 9 and the rib 10 reliably immobilize the abutment means 4 relative to the dental handpiece.

The rib 10 (FIG. 4) of the abutment means 4 extends over a length L2 equal to or slightly less than the length L1 (FIG. 2) of the groove 9, which totally immobilizes the guide support 8 in the groove 9 as shown in FIG. 1. The groove 9 extends along a direction substantially perpendicular to the penetration direction I-I, and the bearing surface 6a of the abutment body 6 being substantially perpendicular to the penetration direction I-I, the forces applied to the abutment means 4 are not such as to cause movement in translation in the engagement direction III-III of the rib 10 in the groove 9. Indeed, the forces applied to the abutment means are substantially in the penetration direction I-I and are therefore perpendicular to the engagement direction III-III in which the groove 9 is oriented. Thus these forces cannot cause movement of the rib 10 in the groove 9.

Moreover, the dovetail joint between the groove 9 and the rib 10 prevents all movement of the abutment means 4 other than translation in the axial engagement direction III-III in which the groove 9 extends.

In FIG. 2, the abutment means have been detached from the dental handpiece to allow the use without impediment of a drill 12 with an abutment shoulder. It is seen that no overall size is added to the dental handpiece when the abutment means have been detached from it. When the abutment means have been detached from the dental handpiece, the dental handpiece has no projecting element in the vicinity of its head 3.

The practitioner can therefore use without impediment a drill 12 with an abutment shoulder or a drill 1 with no abutment shoulder in combination with a surgical guide.

If the case where abutment means 4 are not used, the groove 9 is apparent and undercut because of its trapezoidal cross section in the dental handpiece. To prevent the accumulation of pollutant particles in the groove 9, it is possible to introduce into the groove 9 a plug of exterior shape substantially identical to that of the rib 10. The plug then protects the groove 9 which thus remains clean and free of any element that could prevent or complicate subsequent introduction of the rib 10 into the groove 9 when mounting the abutment means 4 on the dental handpiece.

In the embodiment shown in FIGS. 1 to 7, the dental handpiece includes fluid spray means 13. The fluid spray means 13 include a spray bracket 14 fitted with a pipe 15 adapted to spray a fluid in the vicinity of the working area of the drill 1 or 12 in the form of at least one jet of fluid substantially parallel to the drill 1 or 12.

Figure 6:
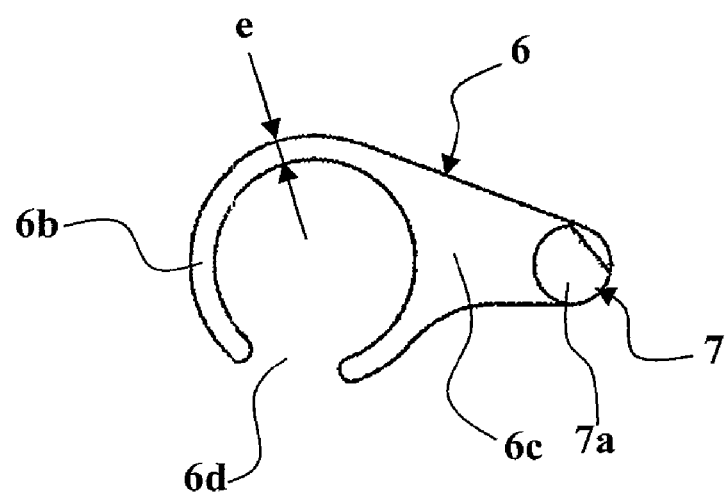
FIG. 6 is a top view of an element of the abutment means of the invention.

In FIG. 6, the abutment body 6 includes around the drill 1 a distal section 6b of annular shape and of small radial thickness e. A connecting bridge 6c extends from the distal section 6b in order to connect it to the connecting section 7.

The abutment body 6 includes an opening 6d in corresponding relationship to the trajectory of the jet of fluid (FIG. 1). This makes the use of the abutment means 4 compatible with the use of fluid spray means to enable the practitioner to work cleanly with a good view of the working area of the drill and under good conditions of hygiene.

In the embodiment shown in FIGS. 1 to 7, abutment means 4 are adjustable and authorize a number of depths P of penetration of the drill 1 into the body of a patient (FIG. 1).

To this end, the connecting section 7 includes a longitudinal connecting rod 7a and the guide support 8 includes a guide sleeve 8a in which the longitudinal connecting rod 7a can slide. Immobilizing means 16 prevent any translation of the longitudinal connecting rod 7a in the guide sleeve 8a.

It is seen more particularly in FIG. 3 that the immobilizing means 16 include a plurality of transverse detents 17 distributed over the length of the longitudinal connecting rod 7a. An immobilizing slider 18, represented in more detail in FIG. 5, comprises a distal end 18a conformed to be engaged in the transverse detents 17 of the longitudinal connecting rod 7a.

Figure 4:
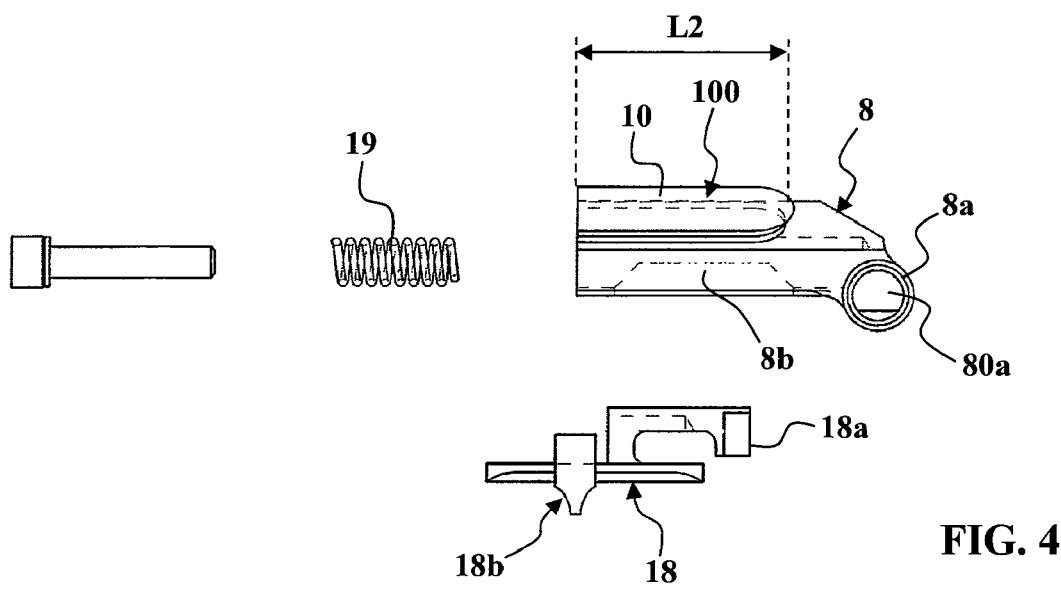
FIG. 4 is an exploded view of various components of the abutment means of the dental handpiece from FIG. 1.
Figure 5:
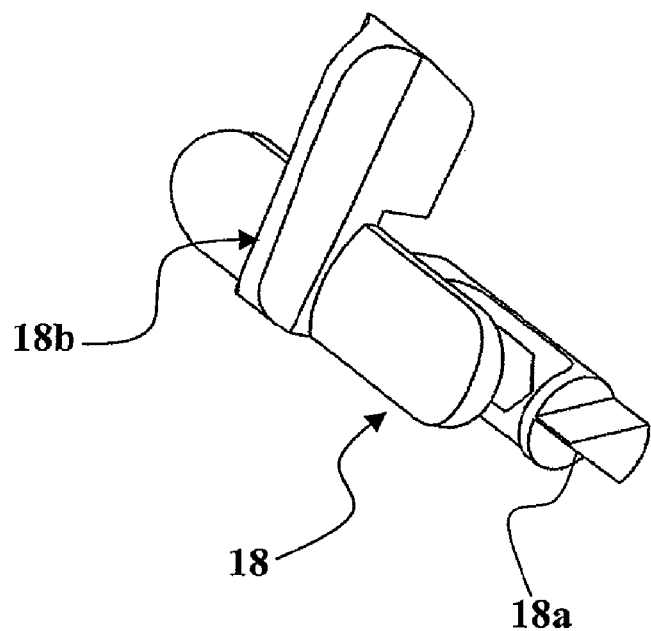
FIG. 5 is a perspective view of an element of the abutment means of the invention.

As shown in FIG. 4, the immobilizing slider 18 is adapted to be mounted in a housing 8b of the guide support 8 to slide laterally towards and away from the longitudinal connecting rod 7a between an immobilizing position in which its distal end 18a is engaged in a transverse detent 17 of the longitudinal connecting rod 7a and a release position in which the distal end 18a of the immobilizing slider 18 is away from the longitudinal connecting rod 7a.

To automate the immobilization of the longitudinal connecting rod 7a in the guide sleeve 8a, a coil spring 19 is provided to urge the immobilizing slider 18 at all times into its immobilizing position. To enable the user to adjust the depth P of penetration, the immobilizing slider 18 includes holding means 18b by which it can be held by a user. As shown in FIG. 1, the holding means 18b enable the user to operate the immobilizing slider 18 in translation in the way and in the direction defined by the arrow 20. Thus the immobilizing slider 18 is operated from its immobilizing position towards its release position against the return force exerted by the coil spring 19. The distal end 18a is then drawn away from the transverse detents 17 of the longitudinal connecting rod 7a which can then be operated in the guide sleeve 8a with a movement of bilateral translation illustrated by the double arrow 21 in order to adjust the depth P of penetration of the drill 1.

If the holding means 18b are released, the immobilizing slider 18 is returned to its immobilizing position by the coil spring 19 to preserve the chosen depth P of penetration.

In order for the abutment body 6 not to come into conflict with the drill 1, it is seen more particularly in FIGS. 4 and 6 that the guide sleeve 8a includes an internal bore 80a with a cross section of complementary shape to the cross section of the longitudinal connecting rod 7a. The cross sections of the longitudinal connecting rod 7a and the internal bore 80a of the guide sleeve 8a prevent all movement in relative rotation between them. For example, in the embodiment illustrated in FIGS. 1 to 7, the cross section of the longitudinal connecting rod 7a is circular with a flat.

The present invention is not limited to the embodiments explicitly described, and includes diverse variants and generalizations thereof within the scope of the following claims.

The invention claimed is:

1. Dental handpiece for carrying a drill (1, 12) and driving it in relative movement in a penetration direction (I-I), comprising:
    a body (2) with a proximal body end (2a) and a distal body end (2b),
    a demountable head (3), connected to the distal body end (2b), and adapted to hold the drill (1, 12),
    abutment means (4) fixed to the dental handpiece by fixing means (5) to limit the depth of penetration of the drill (1, 12) into the body of a patient,
    wherein the abutment means (4) comprise:
    an abutment body (6) with a bearing surface (6a) adapted to bear against the body of the patient at the end of penetration of the drill (1, 12) into the body of the patient,
    a connecting section (7), fastened to the abutment body (6) and extending in a direction (II-II) substantially perpendicular to the bearing surface (6a),
    a guide support (8) forming a projection on the dental handpiece, adapted to hold the connecting section (7), detachably fixed to the dental handpiece,
    wherein:
    the fixing means (5) comprise a female cavity (90) produced in the dental handpiece,
    the fixing means (5) comprise a male protuberance (100), fastened to the abutment means (4), conformed to penetrate and to be retained in the female cavity (90),
    the dental handpiece includes locking means (50) that selectively prevent separation of the male protuberance (100) and the female cavity (90) and are actuated by the simple movement of assembling the head (3) onto the body (2),
    wherein the head (3) is removably fixed to the distal end (2b) of the body (2) by axial engagement in the distal end (2b) of the body (2) along an engagement direction (III-III),
    the female cavity (90) is produced on the head (3), the female cavity having a length L1, oriented axially in the engagement direction (III-III), the female cavity being opened at a proximal end (9a),
    the locking means (50) comprise an abutment facet (51), disposed at the distal end (2b) of the body (2), which blocks the proximal end (9a) of the female cavity (90) when the head (3) has been assembled onto the body (2),
    the male protuberance (100) of the fixing means (5) extends over a length (L2) equal to or slightly less than the length (L1) of the female cavity (90).

2. Dental handpiece according to claim 1, wherein the female cavity (90) is produced in the vicinity of the head (3) and is conformed to enable engagement of the male protuberance (100) in the engagement direction (III-III) substantially perpendicular to the penetration direction (I-I) and to prevent all extraction of the male protuberance (100) in any direction other than the engagement direction (III-III).

3. Dental handpiece according to claim 1, wherein the guide support (8) is entirely detachable from the dental handpiece.

4. Dental handpiece according to claim 1, wherein the female cavity (90) is a groove (9) and in that the male protuberance (100) is a rib (10).

5. Dental handpiece according to claim 4, wherein the groove (9) and the rib (10) have trapezoidal cross sections of complementary shapes allowing to constitute a dovetail joint.

6. Dental handpiece according to claim 1, wherein:
    the dental handpiece includes fluid spray means (13) adapted to spray a fluid in the vicinity of a working area of the drill (1, 12) in the form of at least one jet of fluid having a trajectory substantially parallel to the drill (1, 12),
    the abutment body (6) includes an opening (6d) in corresponding relationship to the trajectory of the jet of fluid.

7. Dental handpiece according to claim 1, wherein:
    the connecting section (7) includes a longitudinal connecting rod (7a),
    the guide support (8) includes a guide sleeve (8a) in which the longitudinal connecting rod (7a) can slide,
    immobilizing means (16) prevent any translation of the longitudinal connecting rod (7a) in the guide sleeve (8a).

8. Dental handpiece according to claim 7, wherein:
    the guide sleeve (8a) includes an internal bore (80a) with a cross section of complementary shape to the cross section of the longitudinal connecting rod (7a),
    the cross sections of the longitudinal connecting rod (7a) and the internal bore (80a) of the guide sleeve (8a) prevent all movement in relative rotation between them.

9. Dental handpiece according to claim 7, wherein the immobilizing means (16) include:
    a plurality of transverse detents (17) distributed over the length of the longitudinal connecting rod (7a),
    an immobilizing slider (18), with a distal end (18a) conformed to engage in the transverse detents (17) of the longitudinal connecting rod (7a), adapted to slide laterally towards and away from the longitudinal connecting rod (7a) in a housing (8b) of the guide support (8) between an immobilizing position in which the distal end (18a) of the immobilizing slider (18) is engaged in a transverse detent (17) of the longitudinal connecting rod (7a) and a release position in which the distal end (18a) of the immobilizing slider (18) is away from the longitudinal connecting rod (7a).

10. Dental handpiece according to claim 9, wherein:
    a coil spring (19) permanently urges the immobilizing slider (18) into its immobilizing position by exerting a return force,
    the immobilizing slider (18) includes holding means (18b) for a user to hold it by, enabling the user to operate the immobilizing slider (18) from its immobilizing position to its release position against the return force exerted by the coil spring (19).

* * * * *